United States Patent [19]

Zhang et al.

[11] Patent Number: 5,556,953
[45] Date of Patent: Sep. 17, 1996

[54] ALLERGEN OF *DOSPORIUM HERBARUM*

[75] Inventors: Lei Zhang, Ottawa; Hari M. Vijay, Gloucester; Harold Rode, Ottawa, all of Canada

[73] Assignee: Minister of Health & Welfare Canada, Ottawa, Canada

[21] Appl. No.: 185,414

[22] Filed: Jan. 24, 1994

[51] Int. Cl.$^6$ .......................... C12N 15/31; C12N 15/11; A61K 39/35

[52] U.S. Cl. .................... 536/23.74; 424/275.1; 424/185.1; 935/12; 435/69.3

[58] Field of Search .................. 536/23.74; 435/69.3; 935/12; 424/275.1, 185.1

[56] References Cited

PUBLICATIONS

Newton, C. H. et al. 1990. J. Bacteriol. vol. 172 pp. 579–588.
Walsh, P. J. et al. 1989. Int. Arch. Allergy Appl. Immunol. vol. 90 pp. 78–83.
Landmark, E. et al. 1985. Int. Arch. Allergy Appl. Immunol. vol. 78 pp. 71–76.
Aukrust, L. et al. 1979. Int Arch. Allergy Appl. Immunol. vol. 60 pp. 68–79.
Breiteneder, H. et al. 1989. EMBO J. vol. 8 pp. 1935–1938.
Mohapatra, S. S. et al. 1990. Int. Arch. Allergy Appl. Immunol. vol. 91 pp. 362–368.
Vander Heide, S. et al. 1985. Allergy vol. 40 pp. 592–598.
Sward–Nordmo, M. et al. 1989. Int. Arch. Allergy Appl. Immunol. vol. 90 pp. 155–161.
Sward–Nordmo, M. et al. 1985. Int. Arch. Allergy Appl. Immunol. vol. 78 pp. 249–255.

*Primary Examiner*—Mary E. Mosher
*Attorney, Agent, or Firm*—George A. Seaby

[57] ABSTRACT

IgE-mediated atopic diseases induced by airborne protein allergens afflict approximately 20% of the population who suffer from allergic systems such as conjunctivitis, rhinitis and asthma. *Cladosporium herbarum* is one of the major sources of inhalant fungal allergens of this type. This invention provides a novel allergen of the organism *Cladosporium herbarum*, and a method of producing the allergen using recombinant techniques.

2 Claims, 7 Drawing Sheets

```
      C GGC AAA AAC ACC GTC AAG ATG AAG TAC ATG GCA GCT TAC    40
                                  Met Lys Tyr Met Ala Ala Tyr
                                                    5
CTC CTC CTC GGC TTG GCC GGC AAC TCC TCC CCC TCT GCT GAG       82
Leu Leu Leu Gly Leu Ala Gly Asn Ser Ser Pro Ser Ala Glu
        10                  15                  20
GAC ATC AAG ACT GTC CTC AGC TCT GTT GGC ATC GAC GCC GAC       124
Asp Ile Lys Thr Val Leu Ser Ser Val Gly Ile Asp Ala Asp
            25                  30                  35
GAG GAG CGC CTC TCT TCC CTC CTT AAG GAG CTC GAG GGC AAG       166
Glu Glu Arg Leu Ser Ser Leu Leu Lys Glu Leu Glu Gly Lys
                40                  45
GAC ATC AAC GAG CTG ATC TCT TCC GGC TCC CAG AAG CTT GCC       208
Asp Ile Asn Glu Leu Ile Ser Ser Gly Ser Gln Lys Leu Ala
 50                  55                  60
TCC GTT CCC TCC GGT GGC TCT GGC GCC GCC CCC TCT GCT GGT       250
Ser Val Pro Ser Gly Gly Ser Gly Ala Ala Pro Ser Ala Gly
     65                  70                  75
GGT GCC GCT GCC GCT GGT GGT GCC ACC GAG GCC GCC CCC GAG       292
Gly Ala Ala Ala Ala Gly Gly Ala Thr Glu Ala Ala Pro Glu
         80                  85                  90
GCC GCC AAG GAG GAG GAG AAG GAG GAG TCC GAC GAC GAC ATG       334
Ala Ala Lys Glu Glu Glu Lys Glu Glu Ser Asp Asp Asp Met
             95                  100                 105
GGC TTC GGT CTG TTC GAC TAA GCG CCA ACG CCA ACG ATG GAT       376
Gly Phe Gly Leu Phe Asp
                 110
GCCTGACATG AAAGCCTGGC TTTGGGATGG ACTTTGGTGG ATGAAGGGCG        426

CAAGCAATTC TGCCCCACGG AAGCCGGAGG ACTAGAGGCA TGGCTATGTC        476

GTGGACTCAT TTTTCGCAAG GGTGGAAGTC CGGCGTCTGG TTATGCTCAA        526

AATGAACCTC CTTCATCAGC AAAAAAAAAA AAAAAAAAAA AAAAAAAAAA        576

AAAAAAAAAA AAAAAAAAAA AAAAAAAAAA AAAAAAAAAA AAAAAAAAAA        626

AAAA                                                          630
```

```
C.herbarum  1 MKYMAAYLL--LGLAGNSSPSAEDIKTVLSSVGIDADEERLSSLLK---ELEGKDINEL-
              :  : :::::  : :::::: ::            :: :: ::      :: ::
human       1 MRYVASYLLAALG--GNSSPSAKDIKKILDSVGIEADDDRLN---KVISELNGKNI-EDV 55 ISSGSQKLASVPSGGSGA-APSAG-G-AA-AAGGATEAAPEAAK-E---EEKEESDDDMGFGLFD
              :  ::::::::  : :::::: :                ::::: :::::::::::::::
           55 IAQGIGKLASVPAGG---AVAVSAAPGSAAPAAGSAPAAEEK-KDEKKEESEESDDDMGFGLFD
```

FIG. 7B

```
C.herbarum  1 MKYMAAYLLLGLAGNSSPSAEDIKTVLSSVGIDA-DEERLSSLLKELEGK---DINELISS
              :: ::::::: :::   :::   :: :  ::: ::  :: :: ::      ::
yeast       1 MKYLAAYLLNAAGNT-PDATKIKAILESVGIEIEDEKV-SSVLSALEGKSVD--ELITE 58 GSQKLASVPSGGSGAA-P-SAGGAAAAGG-ATEAAPEAAKEEEK--EESDDDMGFGLFD
              : :: ::::  ::::::::                :::::::::::::::::::
           57 GNEKLAAVP------AAGPASAGGAAAASGDA--AAEEE-KEEEAAEESDDDMGFGLFD
```

ALLERGEN OF *DOSPORIUM HERBARUM*

BACKGROUND OF THE INVENTION

1. Field of the Invention

This invention relates to an allergen of *Cladosporium herbarum*, and specifically allergenic protein of *Cladosporium herbarum*.

2. Discussion of the Prior Art

IgE-mediated atopic diseases induced by airborne protein allergens afflict 20% of the population who suffer from allergic symptoms such as conjunctivitis, rhinitis, and asthma. The airborne allergens originate from a variety of sources including pollens of grasses, weeds and trees, spores of mold, faeces of mites, and danders of pets and domestic animals. Molecular characterization of the allergens is essential to understand the mechanisms of the specific IgE antibody induction, and the pathogenesis of the diseases, and the development of more efficacious and specific diagnostic and therapeutic methods.

Progress in characterization of the allergens has been slow until the recent employment of gene cloning and expression techniques in allergen research. A number of allergens have been cloned and sequenced from pollens of grasses (Silvanovich A, Astwood J, Zhang L, et al. *J. Bio. Chem.* 266:1204, 1991); trees (Breiteneder H, Pettenburger K, Bito A, et al. *EMBO J.* 8:1935, 1989); weeds (Rafnar T, Griffith IJ, Kuo MC, et al. *J Bio Chem.* 266:1229, 1991); dust mites (Chua KY, Greene WK, Kehal P, Thomus W. *Clin. Exp. Allergy.* 21:161, 1991); insects (Fang, K. S. Y., Vitale, M., Felner, P., King, T. P. *Proc. Natl. Acad. Sci. USA.* 85:895, 1988) and animals (Griffith IJ, Craig S, Pollock J, et al. *Gene.* 113:263, 1992). The availability of the amino acid sequences of the allergens has facilitated (i) the determination of their biological functions, (ii) the analysis of their T- and B-cell epitope, and (iii) an increase in knowledge of the pathogenesis of the diseases. Moreover, such cloned genes can be used to provide unlimited quantities of purified allergenic molecules.

GENERAL DESCRIPTION OF THE INVENTION

It has been determined that *Cladosporium herbarum* (*C. herbarum*) is one of the major sources of inhalant fungal allergens (Hoffman, R. D. Mould allergens; in Al-Doory, Domson, *Mould allergy.*. Lea & Febiger, Philadelphia, 1984 and Solomon W. R. Pollens and fungi; in Middleton E., Reed C. E., Ellis E. F. (eds): Allergy: Principles and Practice. St. Louis, Mosby, 1978). Because only minute amounts of the allergenic components are present in the extract of the organism, it is almost impossible to investigate their molecular features further by conventional means.

An object of the present invention is to provide a novel allergen of the organism *Cladosporium herbarum*, and to analyze the sequence of the allergen.

Another object of the invention is to provide a method of producing the allergen using recombinant techniques.

Thus according to one aspect the invention relates to a nucleic acid sequence coding for the allergen Ch 2.1 of *Cladosporium herbarum* or at least one antigenic fragment thereof.

According to another aspect the invention relates to a method of producing the allergen Ch 2.1 of *Cladosporium herbarum* or at least one antigenic fragment thereof comprising the steps of culturing a host cell transformed with a DNA sequence encoding *Cladosporium herbarum* allergen Ch 2.1 or a fragment thereof in an appropriate medium to produce a mixture of cells and medium and purifying said mixture to produce substantially pure *Cladosporium herbarum* allergen Ch 2.1.

According to yet another aspect the invention relates to a purified protein produced by recombinant DNA techniques that has a molecular weight of 11.12 kDa.

BRIEF DESCRIPTION OF THE DRAWINGS

The invention will be described in greater detail with reference to the accompanying drawings, wherein:

FIG. 11 shows the partially purified 53.6 kDa recombinant allergen and its reaction with human IgE antibodies.

DESCRIPTION OF PREFERRED EMBODIMENT

Isolation of RNA molecules from culture of *C. herbarum*

An isolate, IMI 26229, of *C. herbarum* was cultured on liquid synthetic revised tobacco medium at 22° C. using the method of Vijay H., Burtton M., Young N. M., Copeland D. F. and Corlett M.(see *Grana.* 30:161, 1991). The mycelia were harvested at day 7, 15, and 23, respectively. After three washes with sterile ice-cold PBS, the mycelia were dried and stored at −70° C. The mycelial mass was ground in a mortar and pestle under liquid nitrogen. The powder was suspended in 4.7 of mol/L guanidine isothiocyanate containing 1% β-mercaptoethonal and homogenized with Polytron, followed by the addition of N-lauroylsarcosine to a final concentration of 0.1%. The debris was removed by centrifugation at 10,000 rpm for 10 minutes. The supernatant was layered on top of 5.7 mol/L of cesium chloride and subjected to ultracentrifugation at 25,000 rpm with an SW28 rotor for 24 hours. The RNA pellets were extracted twice with phenol/chloroform and precipitated with sodium acetate and ethanol. After determination of quantities of the RNA, equal amounts of the three different time culture were pooled.

Establishment of a unidirectional cDNA library

A cDNA expression library was constructed in Lambda ZAP II vector (Strategy, CA) with Poly A RNA isolated from the total RNA isolated from the total RNA pool by oligo dT cellulose chromatography [Aviv H. and Leder P. *Pro. Natl.*

Acad. Sci. USA. 69:1408, 1972). The first strand DNA molecules were synthesized using primer XhoI(dT)$_{15}$ and reverse transcriptase, followed by using DNA polymerase and RNase H to synthesize the second strand DNA. The potential EcoR1 sites of DNA molecules were methylated before ligation with EcoR1 adaptors. Double digestion of both cDNA molecules and the vector was achieved with EcoR1 and Xho1. The cDNA was ligated into Lambda ZAP II vector. The *E. coli* strain XL1-blue was used as host for amplification and screening of the library.

Screening of the cDNA library with human IgE antibodies

The cDNA library was screened using human IgE antibodies specific to *C. herbarum*. The IgE antibody preparation was a mixture of equal volumes of sera from 6 patients highly allergic to *C. herbarum* as determined by skin test and direct RAST Vijay H., Burtton M., Young N. M., Copeland D. F., Corlett M. Grana. 30:161, 1991). Sera from six non-mold allergic individuals were also pooled and used as a negative control. *E. coli* XL1-blue cells were infected with phage particles and plated on Luria-Bertani (LB) agar in petri plates. Each plate of 90 mm diameter was plated with approximately 5×10$^3$ phages and incubated at 42° C. for 4 hours. Nitrocellulose filters (Schleicher & Schuell, N.H.) presoaked with 10 mmol/L isopropyl-β-D-thiogalactopyranoside (IPTG, BRL, ONT.) were layered on the top agar and incubated at 37° C. for 3.5 hours. The filters were lifted and washed for 3×5 minutes with Tris-buffer saline containing 0.5% Tween 20* (TBST). After saturation with 3% blocking reagent (Boehringer Mannheim, QUE) at room temperature overnight, the filters were incubated at room temperature overnight 1 in 5 dilution of the serum pool preabsorbed with the extract of *E. coli*. The plaques recognized by the IgE antibodies were detected by 1:2,000 dilution of a conjugate of alkaline phosphatase and goat anti-human IgE antibodies (Sigma, Mo.) and substrates NBT and BCIP.

Subcloning and conversion of the phage into plasmid

The positive clones were isolated, replated, and rescreened until to yield pure clones. *E. coli* XL1-blue cells of overnight growth were co-infected by the cloned Lambda phage and helper phage (Strategen, Calif.). The cells were incubated at 37° C. for 15 minutes followed by incubation with vigorous shaking at 37° C. for 5 hours. The supernatant was collected by centrifugation at 5,000 rpm for 10 minutes and

*Trademark used to infect overnight growth XL1-blue cells. The bacterial colonies containing plasmid were obtained by overnight culture of the infected cells on ampicillin LB agar plates.

DNA sequencing of the cDNA insert

Double strand plasmid DNA was used as template for DNA sequencing. The plasmid was isolated from an overnight culture of the XL1-blue cells using a Magic Miniprep Kit (Promega, Wis.). Asymmetric PCR was performed to produce different lengths of single strand DNA using 5'-Fluorescein labelled M13 reverse primer, Tth DNA polymerase, and dNTP and ddNTP (Sanger F, Nicklen S and Coulson AR, *Proc Natl Acad Sci USA* 74:5463, 1977) provided in Pharmacia Auto-Cycle Kit (Pharmacia, QUE.). The cycle of PCR was 95° C. for 36 seconds, 50° C. for 36 seconds, and 72° C. for 84 seconds, with total of 25 cycles. A strategy of primer walks was employed for continuation of sequencing. The primers were Fluorescein-AGAAGCTTGC|CTCCGTTCCC (SEQ ID NO: 5) and Fluorescein-AGGAGGAGTC|CGACG (SEQ ID NO: 6), which were synthesized using Cyclone Plus DNA Synthesizer (Millipore, Ma.). For the ambuity caused by GC rich regions, higher annealing temperature (60° C. and 65° C.) was used. All the sequences were read and recorded by an automate ALF DNA sequencer (Pharmacia, QUE). The cDNA sequence and deduced amino acid sequence were analyzed using DNAsis and Prosis programs (Hitachi, Calif.), respectively.

Northern Blotting

Total RNA of 20 μg from *C. herbarum* mycelia was electrophoresed in the presence of formamide in 1.2% agarose/formaldehyde gel. The separated RNA molecules were electrotransferred onto Hybond-N membrane (Armershan, ONT.) using TAE buffer having a pH of 7.5, followed by UV crosslinking using UV Stratalinker* (Strategene, Calif.). The membrane was blocked in hybridization solution: 5X SSC, 1% blocking reagent (Boehringer Mannhein, QUE), 0.1% N-lauroylsarcosine, and 0.2% SDS at 65° C. for 2 hours. $^{32}$P-dATP was incorporated in the insert DNA using a Random Primer Labelling Kit (Promega, Wis.) (Feinberg FW and Vogelstein B. *Anal Biochem.* 132:6, 1983), and the probe was incubated with the membrane at 65° C. overnight. The membrane was washed 2×5 minutes at room temperature with 2×SSC, 0.1% SDS, and then 2× 15 minutes at 65° C. with 0.1×SC and 0.1% SDS. After the membrane dried at room temperature, the blot was autoradiographed.

Expression of the cloned allergen

The full-length clone Ch2.1 was amplified by PCR using a pair of primers, GAATTCTCCG|GCAAAAACAC|CGTCAAGATG )SEQ ID NO: 7) and CTGCAGAATA|CGACTCACTATA|GGGCG (SEQ ID NO: 8) designed according to the DNA sequence. The amplified fragments were subcloned into TA vector (Invetrogen, Calif.). The isolated plasmid was digested using EcoR1 and Pst1 to release the insert, followed by ligation into expression vector pMAL-c2 (New England Biolab, Ma.), which was also prepared with EcoR1 and Pst1 digestion. The procedure for induction and analysis of the fusion protein was according to the manufacturer's instruction. Briefly, TB1 cells were transformed by the recombinant plasmid vectors and

*Trademark plated on ampicillin-containing LB agar. Single colonies were picked to inoculate LB-ampicillin media and grown overnight at 37° C. LB media containing 0.2% glucose and ampicillin was inoculated with the overnight growth culture at ratio of 1:100 (v/v) and incubated at 37° C. IPTG was added to induce synthesis of the fusion protein when the cell density reached about 0.5 of A$_{600}$. The fusion protein was analyzed by SDS-PAGE and IgE immunoblot. Partial purification of the fusion protein was achieved using amylose-resin provided by New England Biolab and SDS-PAGE electrophoresis.

Identification and isolation of a cDNA clone

Figure 1:
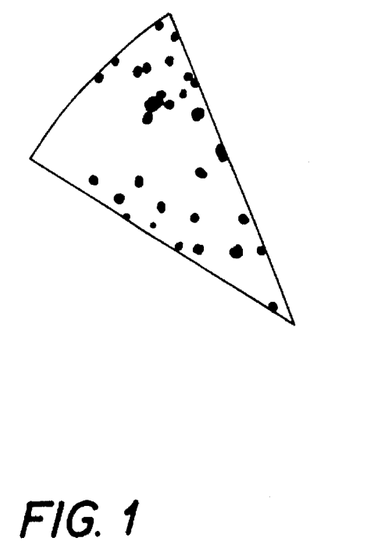
FIG. 1 shows the results of the reaction of plaques of an allergen-synthesizing cDNA clone with human IgE antibodies.
Figure 2:
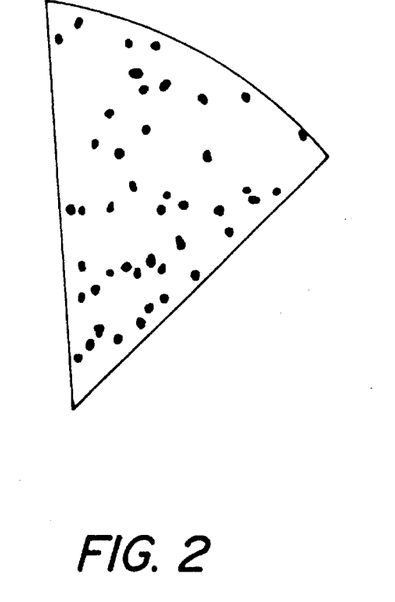
FIG. 2 shows results similar to FIG. 1 for a normal serum pool with or without antibodies.
Figure 2:
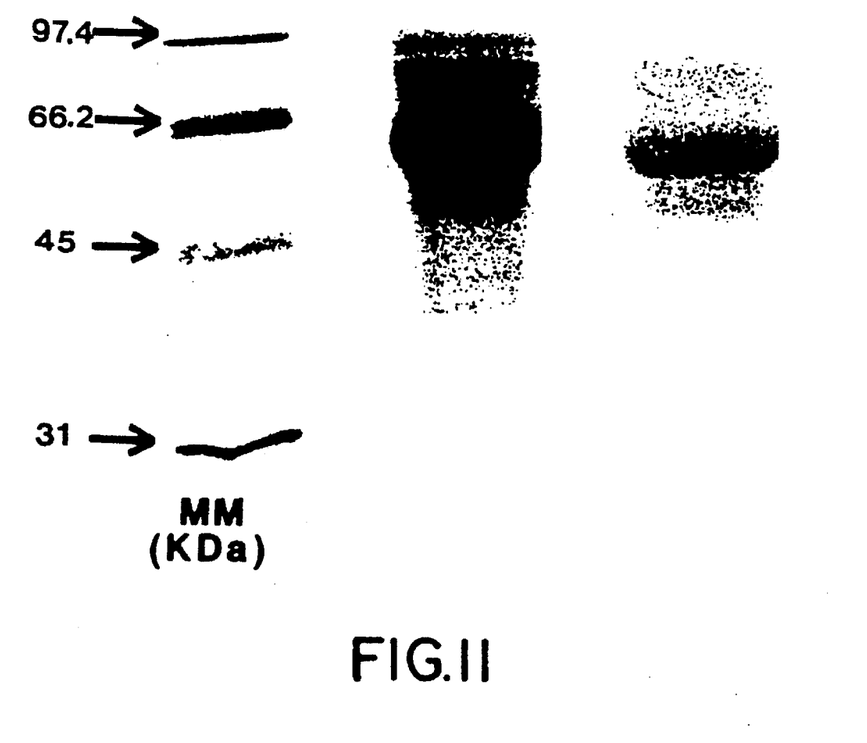
Figure 3:
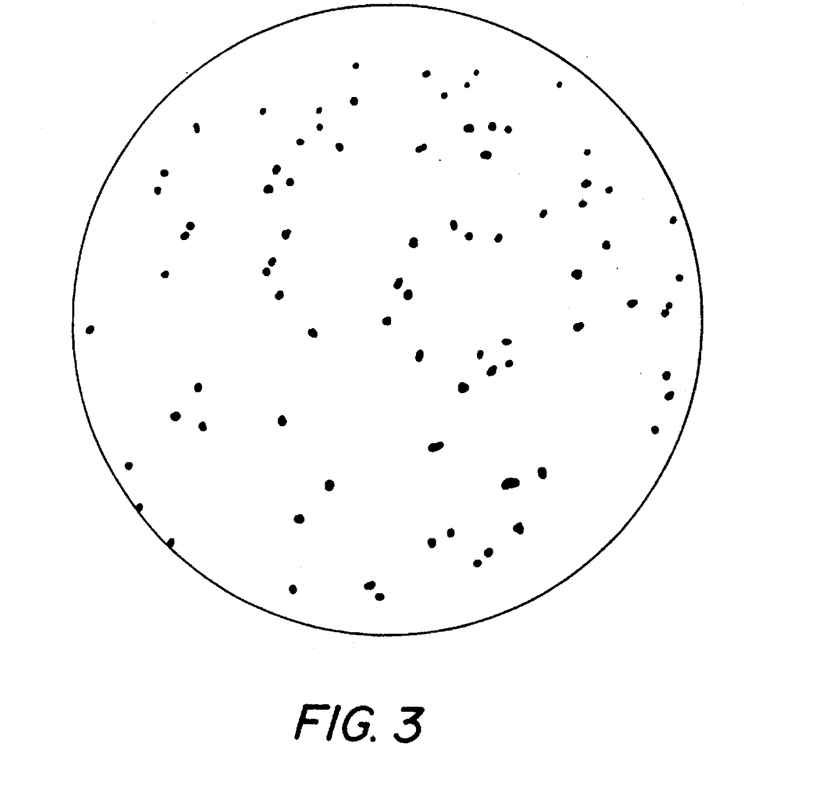
FIG. 3 illustrates the results of the reaction of plaques of a purified cDNA clone with human IgE antibodies.

The cDNA library was screened with the serum pool from the atopic individuals. One clone, designated as Ch2.1, was initially found to react with human IgE antibodies using alkaline phosphatase and goat anti-human IgE conjugate and the substrate by color reaction. Confirmation of its IgE binding activity was made by employment of $^{125}$I-labelled anti-human IgE antibodies. The partially purified clones detected by the isotype-labelled anti-human IgE showed the clear comparison that the plaques of the allergen-synthesizing clone, but not of the clones synthesizing other non-allergenic proteins, reacted with the human IgE antibodies (FIG. 1a). The normal serum pool showed no binding to plaques, which did or did not contain the allergens (FIG. 2). After three times of isolation, replating, and rescreening, a purified clone was obtained. All the plaques of the clone demonstrated a uniform reactivity to human IgE antibodies (FIG. 1).

Analysis of the cDNA insert

Figure 4:
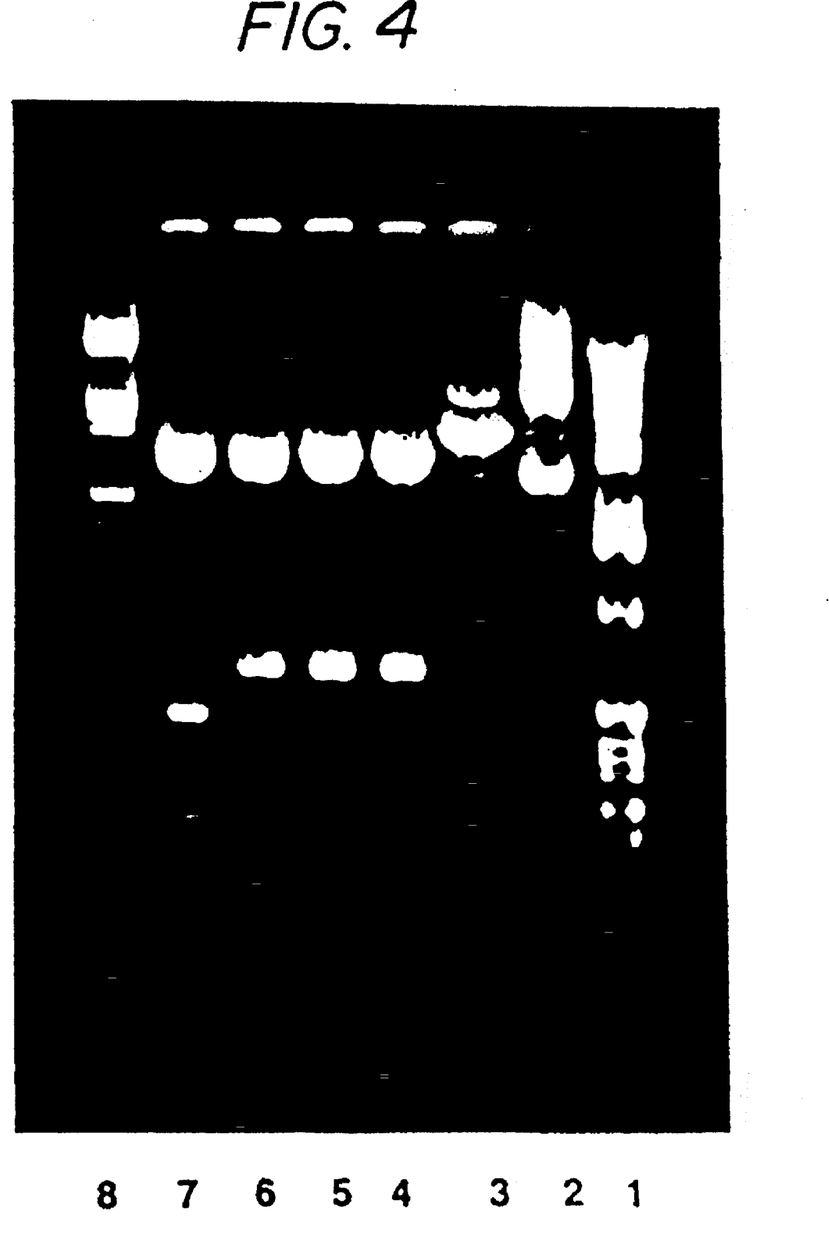
FIG. 4 illustrates the results of restriction analysis of cDNA insert.
Figure 5:
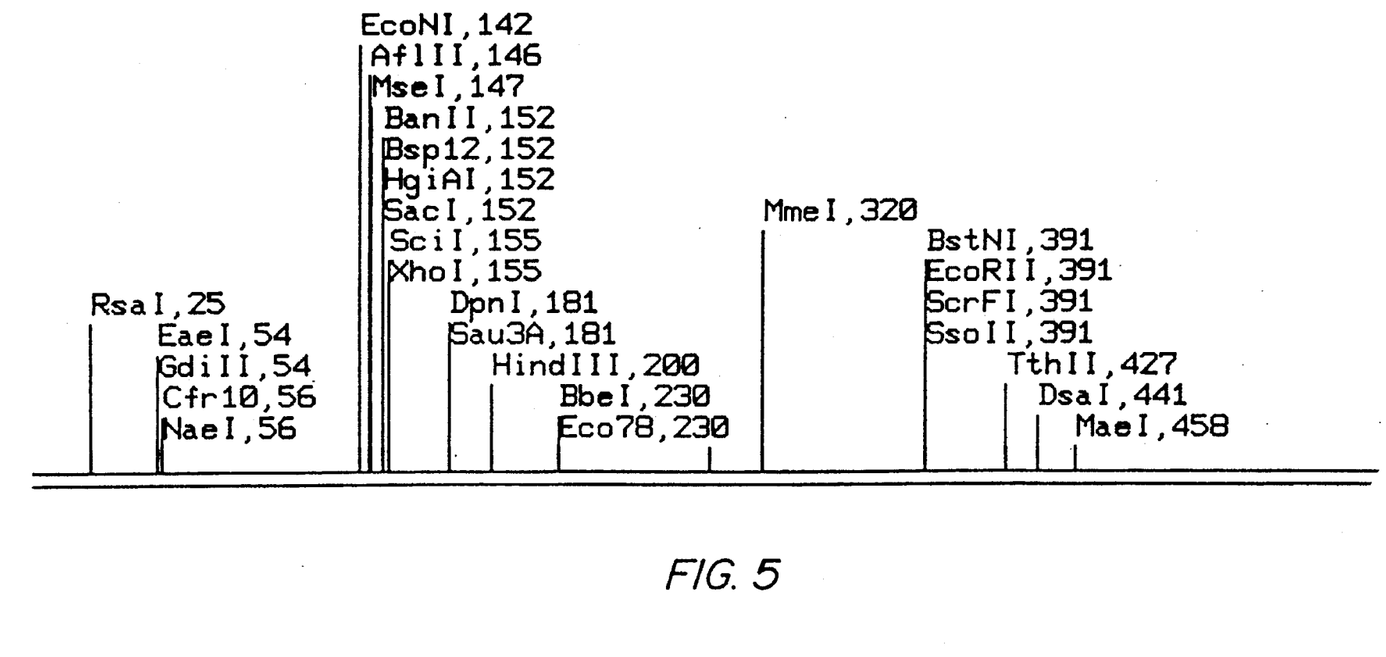
FIG. 5 is the restriction map of the cDNA insert.

The cloned phage DNA was converted into phagemid with aid of helper phage. The phagemid DNA isolated from the host cells was analyzed by digestion with restriction enzymes. The results showed that the cDNA isnert was about 650 bp in length, and had a XhoI site but no ApaI, EcoR0109I, and KpnI sites (FIG. 4). The major restriction sites of the Ch2.1 cDNA insert obtained form its DNA sequence analysis are shown in FIG. 5.

Sequence of the cDNA clone and its deduced amino acid sequence

Figure 6:
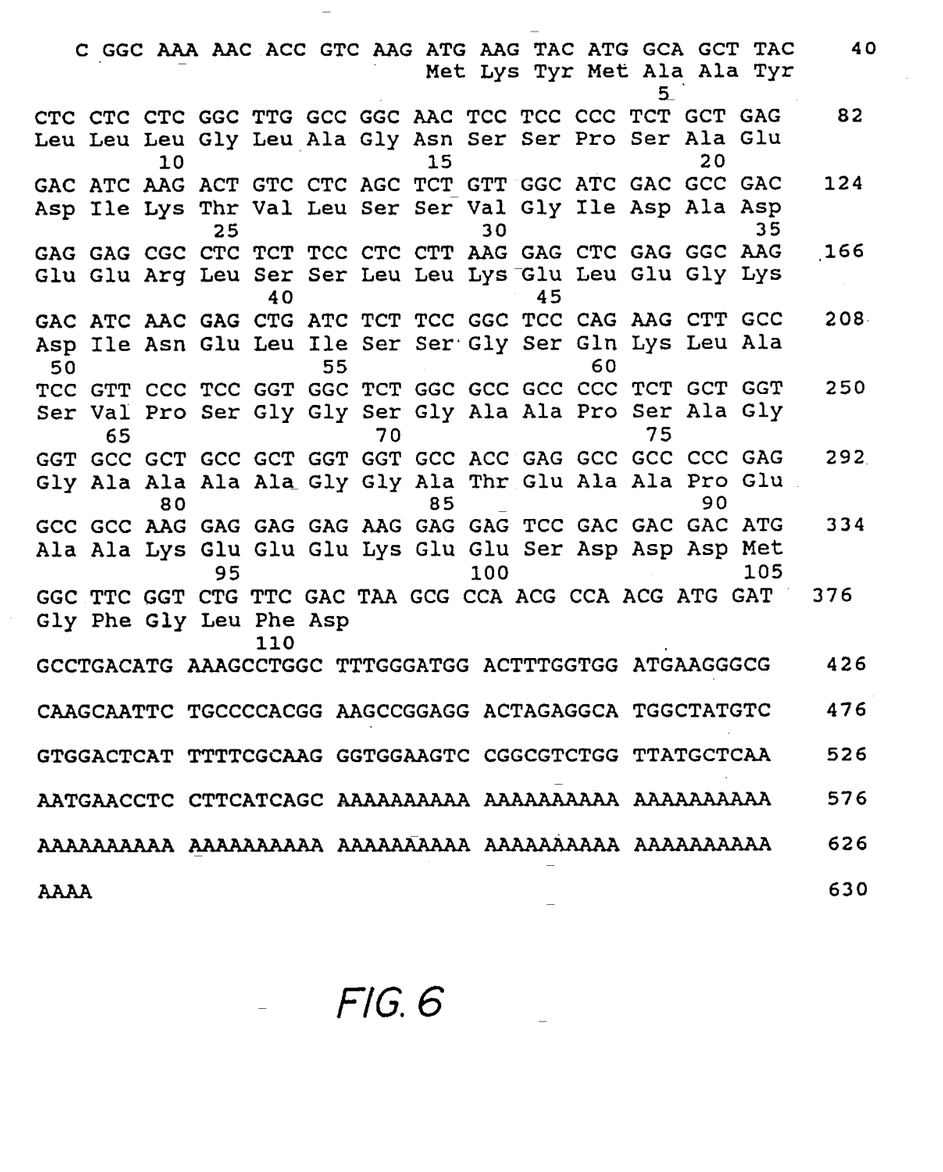
FIG. 6 shows the DNA sequence (SEQ ID NO: 1) and amino acid sequence (SEQ ID NO: 2) of the cloned allergen Ch 2.1 of *Cladosporium herbarum*.

The DNA sequence of cDNA Ch2.1 is shown in FIG. 6 (SEQ ID NO: 1). The insert is 630 base pairs in length and possesses features indicating it contains a full-length coding sequence. DNA sequence analysis revealed that the cDNA contains several potential start codons, but only the ones in phase with the open reading frame (ORF) of the β-galactosidase gene of λ-ZAP II vector are correct since it produced immunoreactive fusion proteins detected by the human IgE antibodies. Two such potential start condons are found in this clone, one is at the position of 20 bases and the other at 27 bases. The first one was considered to be the right start codon according to the results of protein sequence homology described below. This clone has a complete 3' nontranslated region with a poly(A) tail. The possible polyadenylation signal AATGAA (Birnstiel ML, Busslinger M, and Srub K. Cell. 41:349, 1985) is found at the position of 13 bases upstream of the poly(A).

The deduced protein is 111 amino acid residues in length, and its molecular weight is calculated to be 11.12 kDa. The amino acid composition (Table 1) of this protein is rich in alanine (16.2%), serine (13.5%), glycine (12.5%), glutamic acid (11.7%), and leucine (10.8%).

TABLE 1

Amino acid composition
Amino Acid Count Mol %

| Gly | G | 14 | 12.61 |
| --- | --- | --- | --- |
| Ala | A | 18 | 16.22 |
| Val | V | 3 | 2.70 |
| Leu | L | 12 | 10.81 |
| Ile | I | 4 | 3.60 |
| Ser | S | 15 | 13.51 |
| Thr | T | 2 | 1.80 |
| Cys | C | 0 | 0.00 |
| Met | M | 3 | 2.70 |
| Asp | D | 8 | 7.21 |
| Asn | N | 2 | 1.80 |
| Glu | E | 13 | 11.71 |
| Gln | Q | 1 | 0.90 |
| Arg | R | 1 | 0.90 |
| Lys | K | 7 | 6.31 |
| His | H | 0 | 0.00 |
| Phe | F | 2 | 1.80 |
| Tyr | Y | 2 | 1.80 |
| Trp | W | 0 | 0.00 |
| Pro | P | 4 | 3.60 |
| Asx | B | 0 | 0.00 |
| Glx | Z | 0 | 0.00 |
| *** | * | 0 | 0.00 |
| Xxx | X | 0 | 0.00 |

(Total 111)

Figure 7A:
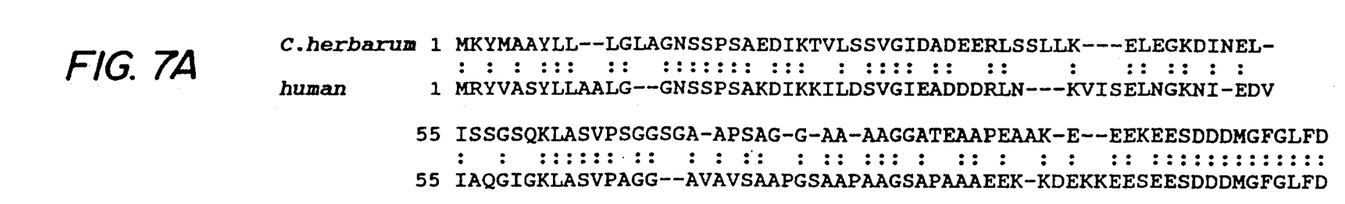
FIGS. 7A and 7B show the results of homology analysis of the protein sequence of cDNA clone (SEQ ID NO: 2) with human (SEQ ID NO: 3) and yeast (SEQ ID NO: 4) ribosomal $P_2$ proteins, respectively.
Figure 7B:
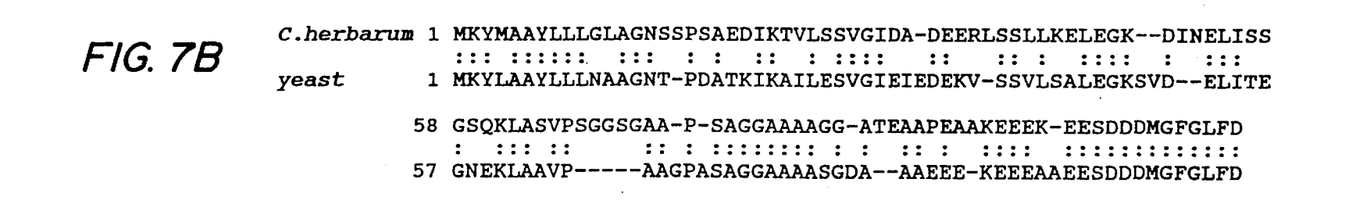

There is a potential N-glycosylation site at residues 15–17 in the hydrophillic region showing the characteristic Asn-x-Ser/Thr motif. Homology analysis of the protein sequence with all known sequences in the NBRF-PIR protein sequence data bank revealed that it belongs to the ribosomal acidic protein family. The sequence identities to human (Rich BE and Steitz JA. Mol Cell Biol. 7:4065, 1987) and yeast (Saccharomyces cereviae) (Remach M, Saenz-Robles MT, Vilella MD, and Ballesta JPG. J Biol Chem. 263:9094, 1988) ribosomal P$_2$ proteins are 60% and 61%, respectively (FIGS. 7A and 7B). The consensus C-terminal sequence (13 amino acid residues) of the ribosomal P$_2$ proteins was found in this cloned allergen. The relatively conserved N-terminal region (9 amino acid residues) in the allergen was almost identical to the yeast protein.

Hydropathic profile of the protein

Figure 8:
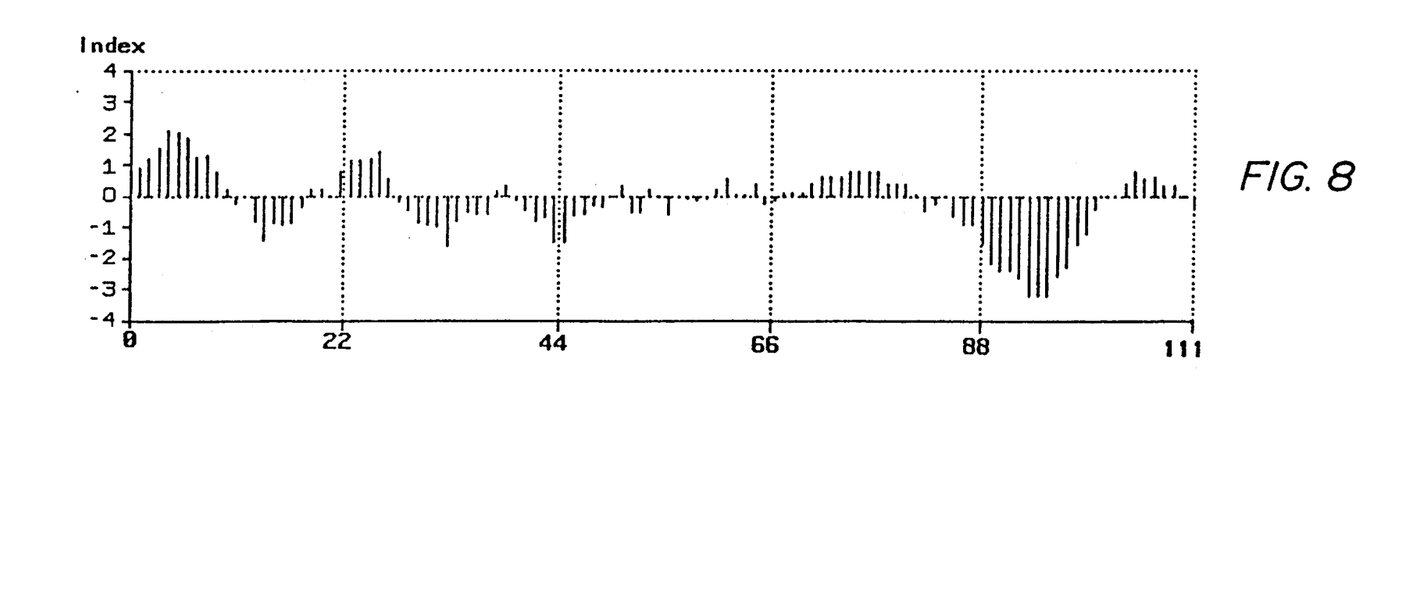
FIG. 8 is the hydropathic profile of the deduced amino acid sequence.

The hydropathic profile of the allergenic protein was analyzed using the Kyte and Doolittle method (Kyte J. and Doolittle RF. J Mol Biol. 157:105, 1982) with a window of six amino acids (FIG. 8). The most hydrophillic region of the allergen was located at its C-terminal sequence. A few other hydrophillic regions distributed on its N-terminal half sequence. These areas may also represent the potential anti-body-binding sites. At its N-terminus, an amphipathic sequence was illustrated, which may possess a T cell epitope.

Northern blotting analysis

Figure 9:
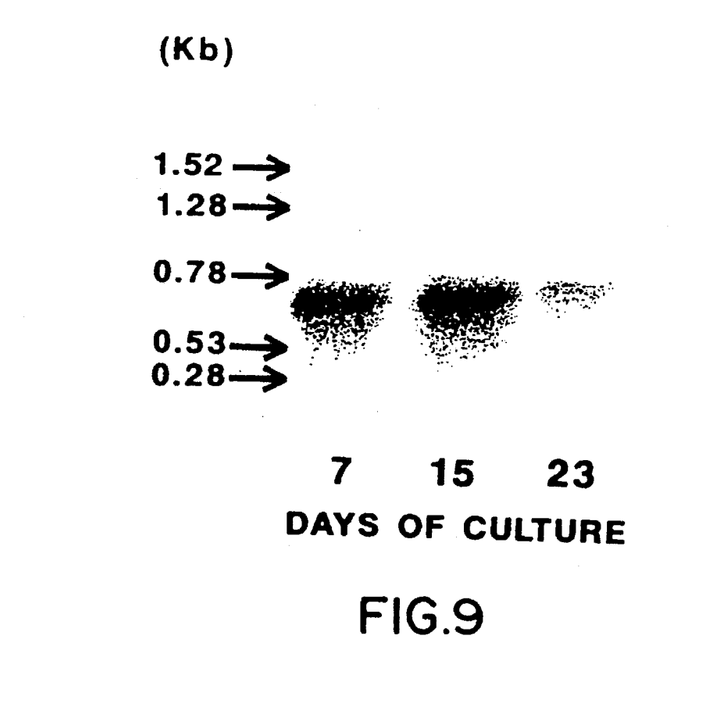
FIG. 9 provides the resultes of Northern blot analysis of the RNA extracted at different culture times.

Northern blotting analysis of the RNA extracted at different culture time demonstrated that the cloned cDNA probe hybridized with a single mRNA band (FIG. 9). The size of the gene coding for the allergen was estimated to be about 720 bases. The gene expression level seemed to be lower at day 23 than that at day 7 and 15. The result also indicated that there was about 90 bases of the 5' nontranslated region missed, although the cDNA contains the sequence coding for the full-length allergen according to the above sequence analysis.

Expression of the recombinant allergen in E. coli

Figure 10:
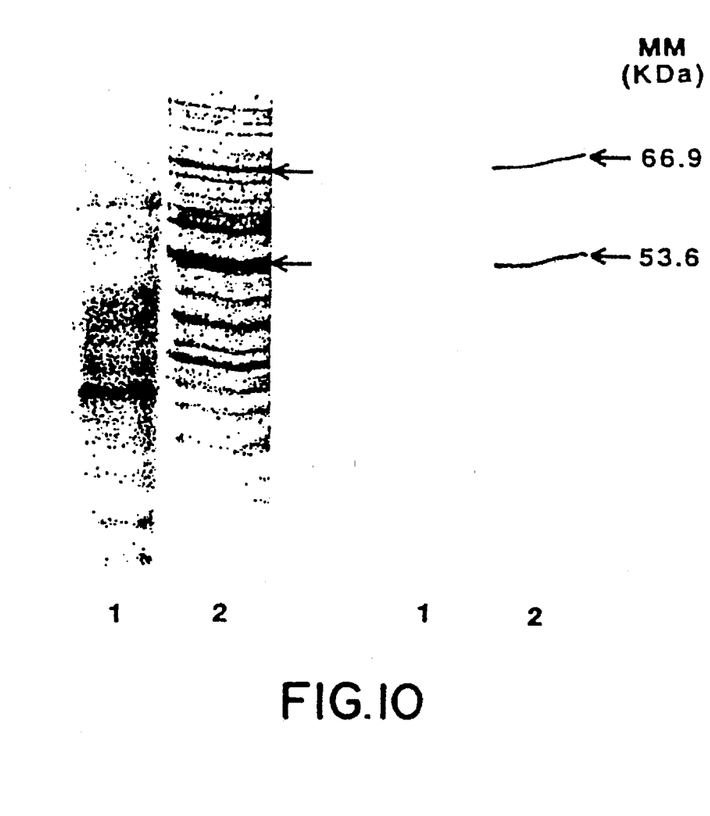
FIG. 10 illustrates the expression of recombinant allergen and molecular weight of the fusion protein.

The recombinant allergen in a form of a fusion protein associated with maltose-binding protein was synthesized in E. coli by gene expression procedures. FIG. 10 shows the Coomassie Blue stain of the expressed protein, which was observed in the E. coli cells transformed with expression vector containing the cDNA insert but not in the non-transformed cells nor in the transformants with the non-recombinant vector. The vector transformed cells expressed a high level of the bacterial maltose-binding (BMB-protein but showed no IgE binding. These results indicated that the BMB protein were not recognized by the mold-specific IgE antibodies and there was no cross-reactivity between these two fused polypeptides. The fusion protein, however, demonstrated IgE binding activities (FIG. 10). Two IgE binding bands were found from the transformed cells. One was relatively abundant in the amounts calculated to be 53.6 kDa, and the other was very faint band with 66.9 kDa. Gel electrophoresis was used to isolate the recombinant allergen and above 80% pure allergen corresponding to the lower band was obtained, which again showed strong IgE-binding activity (FIG. 11).

Molecular cloning and characterization of a cDNA clone coding for an allergen of Cladosporium herbarum (CH) is presented herein. Sequence analysis and comparison led to the conclusion that the open reading frame of the gene and its deduced amino acid sequence presented are correct. Because its start codon is in phase with the open reading frame of the β-galactosidase in λ ZAP II vector, the amino acid sequence shares the common features with other ribosomal P$_2$ proteins. The AATGAA at position of 13 bases upstream of the poly(A) seemed to be the polyadenylation signal according to its location, which was reported to be a mutant of the canonical AATTAA polyadenylation signal (Birnstiel ML, Busslinger M, and Srub K. Cell. 41:349, 1985).

There are two potential start condons adjacent to one another in the reading frame. The reason that the first one at position of 20 bases was considered to be the right start condon is the relative conservation of the N-terminal sequences of these ribosomal P$_2$ proteins (Lin A, Wittmann- Liebold B, McNally J, and Wool IG. *J Biol Chem.* 257:9189, 1982). Almost identical 9 amino acids at N-termini were observed between this allergen and one of those know $P_2$ proteins, which was from its closest species *Saccharomyces cereviae*. Even substitutions of these 9 amino acids in other $P_2$ proteins were found to be conservative (Kyte J. and Coolittle RF. *J Mol Biol.* 157:105, 1982). The most remarkable feature of all ribosomal $P_2$ proteins is also shared by this allergen; i.e. the consensus C-terminal sequence of 13 amino acids. Thus, these convincing results suggested that the allergen belongs to the ribosomal $P_2$ protein family.

These ribosomal phosphorylated (P) proteins, also called acidic proteins, seem to be involved in regulation of protein synthesis (Van Agthoven AJ, Maassen JA, and Moller W. *Biochem Biophys Res Commun.* 77:12, 1977 and McConnell WP, and Kaplan NO. *J Siol Chem.* 257:5359, 1982). From a variety of species the proteins have been isolated and characterized. It is expected that during evolution the amino acid sequences of the proteins performing the same function would be conserved. However, sequence diversities of these ribosomal $P_2$ proteins from different species have been revealed (Rich BE and Steitz JA. *Mol Cell Biol.* 7:4065, 1987; Remacha M, Saenz-Robles MT, Vilella MD, and Ballesta JPG. *J Biol Chem.* 263:9094, 1988 and Lin A, Wittmann-Liebold B, McNally J, and Wool IG. *J Biol Chem.* 257:9189, 1982). Biological functions of proteins are based on their molecular structures. The same principle applies also to protein immunogenicities.

To the best of the present inventors' knowledge, this is the first instance that a ribosomal $P_2$ protein has been identified as an allergen. Allergens are the group of antigens which are capable of induction of and binding to IgE antibodies under natural conditions. It is still not clear whether there is any unique structure of the protein allergens, although recent studies indicated that the allergens are different from common antigens in terms of their antibody isotype induction (Wierenga EA, Snoek M, Jansen HM, et al. *J. Immunol.* 147:2942, 1992; Wierenga EA, Snoek M, De Groot C, Chretien I, et al. *J. Immunol.* 144:4651, 1990; Parronchi P, Macchia D, Pccinni M, et al *Proc. Natl. Acad. Sci. USA.* 88:4538, 1991; Deuell B, Arruda LK, Hayden ML, et al *J. Immunol.* 147:96, 1991; Scott P. Natovitz P, Coffman RL, et al. *J. Exp. Med.* 168:1675, 1988; Yamada M, Nakazawa M, and Arizono N. *Immunol.* 78:298, 1993 and Zhang, L, Sehon A. and Mohapatra SS. *Immunol.* 76:158, 1992). The ribosomal $P_2$ proteins from other sources including human have been reported as antigens inducing IgG antibodies (Elkon KB, Parnassa AP, and Foster CL. *J Exp Med.* 162:459, 1985; Schneebaum AB, Singleton JD, West SG, et al. *Am J Med.* 90:54, 1991 and Bonfa E, Golombek SJ, Kaufman LD, et al *Engl J Med.* 317:267, 1987). The cloned protein described herein shares about 60% identical sequence with the other $P_2$ proteins. The different structures of this molecule may contribute to its property of IgE antibody induction. Thus, if there are indeed some structural differences between antigens and allergens, this newly identified allergen will serve a useful molecular model to facilitate the understanding of such a complicated issue.

The antibody binding sites of the allergen was predicted by its hydropathic profile according to the deduced amino acid sequence. The carboxyl terminus shows highly hydrophillic, indicating a location of a B cell epitope (Hoop T, and Woods K. *Proc Natl Acad Sci USA.* 78:3824, 1981). Indeed, previous studies have demonstrated that his consensus sequence could be recognized by antibodies (Towbin H, Ramjoue HP, Kuster H, et al. *Biol Chem.* 257:12709, 1982). Three hydrophillic regions were disclosed on this protein, which may be also the antibody-binding sites. From the profile of the proteins the N-terminus seems to be the potential a T cell epitope. The hydrophobic region immediately followed by a group of hydrophillic amino acids makes the N-terminus amphipathic. This sequential feature has been matched with T cell epitopes (DeLisi C. and Berzofsky JA. *Proc Natl Acad Sci USA.* 82:7048, 1985).

There is convincing evidence that there are at least three ribosomal acid proteins in eucaryotic cells (Rich BE and Steitz JA. *Mol Cell Biol.* 7:4065, 1987, and Remacha M, Saenz-Robles MT, Vilella MD, and Ballesta JPG. *J Biol Chem.* 263:9094). Antigenic similarities have been reported, especially between ribosomal $P_1$ and $P_2$ proteins. thus, it is difficult to distinguish these two proteins immunologically using either monoclonal antibodies to the consensus carboxyl terminus or the polyclonal antibodies which are available at present. However, the results described herein in which a single transcript band was hybridized with the cDNA probe indicate the feasibility of employing a nucleotide probe to differentiate these two proteins. Moreover, based on the information of the DNA sequences which differ from the ribosomal $P_2$ protein genes of other species, PCR primers can be designed for the identification of this organism.

For the purposes of further characterization of this cloned allergen, the gene was expressed in *E. coli* cells, by which unlimited amounts of purified allergens can be obtained. However, because genes are regulated differently for their expression and possible toxic effect on host cells, various expression systems have to be tried in order to achieve optimal expression level. The allergen expressed here was in the form of fusion protein associated with bacterial maltose-binding (BMB) protein. There were two IgE-binding bands observed in the lysates of the transformants. One band was 53.6 kDa as expected as the molecular weight of the fusion protein (42 kDa for BMB protein and 11.1 kDa for the allergen), while the other was about 66.9 kDa. The reason of appearance of this higher molecular band is not clear at present. There is one possible explanation that the band was formed by the dimers of the allergen. It has been reported that the ribosomal acidic proteins tended to form stable dimers which bind to ribosomal RNA (Gudkov AT and Behlke J. *Eur J Biochem.* 90:309, 1978). In the expression system of this case, since the allergen part of the fusion protein has its own start codon, it was possible that the translation occurred also at this point and to form the free allergen. Thus, even under reduced condition and at presence of SDS the trace of the dimer of this molecule could be detected.

Nevertheless, availability of the recombinant allergen permits the development of a useful reagent for specific diagnosis of the mold allergic disorders. Since the BMB protein showed no IgE binding activities or cross-reaction to the allergen, it will not impede the usefulness of the fusion protein as a diagnostic reagent. Moreover, the fusion protein provided a better immunogen for generation of high titers of the antibodies. The potential of the fusion protein in specific immunotherapy has been indicated from the previous studies (Zhang, L, and Mohapatra SS. *J Immunol.* 151:791, 1993).

The embodiments of the invention in which an exclusive property or privilege is claimed are defined as follows:

1. An isolated nucleic acid comprising a sequence coding for the allergen Ch 2.1 of *Cladosporium herbarum*, wherein said allergen has the amino acid sequence SEQ ID NO:2.

2. An isolated nucleic acid according to claim 1, wherein the nucleic acid sequence comprises the sequence of SEQ ID NO: 1.

* * * * *

UNITED STATES PATENT AND TRADEMARK OFFICE
CERTIFICATE OF CORRECTION

PATENT NO. : 5,556,953

DATED : Sep. 17, 1996

INVENTOR(S) : Lei Zhang et al

It is certified that error appears in the above–identified patent and that said Letters Patent are hereby corrected as shown below:

On the title page, item [54], and in column 1, line 1

Correct spelling error of cladosporium in title. Title should read: ALLERGEN OF *CLADOSPORIUM HERBARUM*

Signed and Sealed this

Tenth Day of March, 1998

Attest:

BRUCE LEHMAN

*Attesting Officer*     Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 630 base pairs
        ( B ) TYPE: nucleic acid
        ( C ) STRANDEDNESS: single
        ( D ) TOPOLOGY: linear     ( i i ) MOLECULE TYPE: cDNA and its encoded protein     ( i i i ) FEATURE: open reading frame of CH2.1

( i v ) SEQUENCE DESCRIPTION: SEQ ID NO: 1:

```
C  GGC  AAA  AAC  ACC  GTC  AAG  ATG  AAG  TAC  ATG  GCA  GCT  TAC              40
                                 Met  Lys  Tyr  Met  Ala  Ala  Tyr
                                                  5

CTC  CTC  CTC  GGC  TTG  GCC  GGC  AAC  TCC  TCC  CCC  TCT  GCT  GAG            82
Leu  Leu  Leu  Gly  Leu  Ala  Gly  Asn  Ser  Ser  Pro  Ser  Ala  Glu
               10                      15                      20

GAC  ATC  AAG  ACT  GTC  CTC  AGC  TCT  GTT  GGC  ATC  GAC  GCC  GAC           124
Asp  Ile  Lys  Thr  Val  Leu  Ser  Ser  Val  Gly  Ile  Asp  Ala  Asp
                    25                      30                      35

GAG  GAG  CGC  CTC  TCT  TCC  CTC  CTT  AAG  GAG  CTC  GAG  GGC  AAG           166
Glu  Glu  Arg  Leu  Ser  Ser  Leu  Leu  Lys  Glu  Leu  Glu  Gly  Lys
                         40                      45

GAC  ATC  AAC  GAG  CTG  ATC  TCT  TCC  GGC  TCC  CAG  AAG  CTT  GCC           208
Asp  Ile  Asn  Glu  Leu  Ile  Ser  Ser  Gly  Ser  Gln  Lys  Leu  Ala
50                       55                      60

TCC  GTT  CCC  TCC  GGT  GGC  TCT  GGC  GCC  GCC  CCC  TCT  GCT  GGT           250
Ser  Val  Pro  Ser  Gly  Gly  Ser  Gly  Ala  Ala  Pro  Ser  Ala  Gly
     65                       70                      75

GGT  GCC  GCT  GCC  GCT  GGT  GGT  GCC  ACC  GAG  GCC  GCC  CCC  GAG           292
Gly  Ala  Ala  Ala  Ala  Gly  Gly  Ala  Thr  Glu  Ala  Ala  Pro  Glu
          80                       85                       90

GCC  GCC  AAG  GAG  GAG  GAG  AAG  GAG  GAG  TCC  GAC  GAC  GAC  ATG           334
Ala  Ala  Lys  Glu  Glu  Glu  Lys  Glu  Glu  Ser  Asp  Asp  Asp  Met
               95                      100                     105

GGC  TTC  GGT  CTG  TTC  GAC  TAA  GCG  CCA  ACG  CCA  ACG  ATG  GAT           376
Gly  Phe  Gly  Leu  Phe  Asp
                    110
```

GCCTGACATG AAAGCCTGGC TTTGGGATGG ACTTTGGTGG ATGAAGGGCG     426

CAAGCAATTC TGCCCCACGG AAGCCGGAGG ACTAGAGGCA TGGCTATGTC     476

GTGGACTCAT TTTTCGCAAG GGTGGAAGTC CGGCGTCTGG TTATGCTCAA     526

AATGAACCTC CTTCATCAGC AAAAAAAAA AAAAAAAAA AAAAAAAAA     576

AAAAAAAAA AAAAAAAAA AAAAAAAAA AAAAAAAAA AAAAAAAAA     626

AAAA     630

( 2 ) INFORMATION FOR SEQ ID NO: 2:

( i ) SEQUENCE CHARACTERISTICS:
        ( A ) LENGTH: 111 amino acids
        ( B ) TYPE: amino acid
        ( C ) STRANDEDNESS:
        ( D ) TOPOLOGY: linear     ( i i ) MOLECULE TYPE: protein ( i i i ) FEATURE:
  ( A ) NAME/KEY: Ch2.1 protein
  ( B ) LOCATION: 1..111

( i v ) SEQUENCE DESCRIPTION: SEQ ID NO: 2:

Met Lys Tyr Met Ala Ala Tyr Leu Leu Leu Gly Leu Ala Gly Asn
                 5                  10                 15

Ser Ser Pro Ser Ala Glu Asp Ile Lys Thr Val Leu Ser Ser Val
                20                  25                 30

Gly Ile Asp Ala Asp Glu Glu Arg Leu Ser Ser Leu Leu Lys Glu
                35                  40                 45

Leu Glu Gly Lys Asp Ile Asn Glu Leu Ile Ser Ser Gly Ser Gln
                50                  55                 60

Lys Leu Ala Ser Val Pro Ser Gly Gly Ser Gly Ala Ala Pro Ser
                65                  70                 75

Ala Gly Gly Ala Ala Ala Ala Gly Gly Ala Thr Glu Ala Ala Pro
                80                  85                 90

Glu Ala Ala Lys Glu Glu Glu Lys Glu Glu Ser Asp Asp Asp Met
                95                  100                105

Gly Phe Gly Leu Phe Asp
                110

( 2 ) INFORMATION FOR SEQ ID NO: 3:

( i ) SEQUENCE CHARACTERISTICS:
    ( A ) LENGTH: 115 amino acids
    ( B ) TYPE: amino acid
    ( C ) STRANDEDNESS:
    ( D ) TOPOLOGY: linear ( i i ) MOLECULE TYPE: protein ( i i i ) FEATURE:
    ( A ) NAME/KEY: human ribosomal P2 protein
    ( B ) LOCATION: 1...115

( i v ) SEQUENCE DESCRIPTION: SEQ ID NO: 3:

Met Arg Tyr Val Ala Ser Tyr Leu Leu Ala Ala Leu Gly Gly Asn
                 5                  10                 15

Ser Ser Pro Ser Ala Lys Asp Ile Lys Lys Ile Leu Asp Ser Val
                20                  25                 30

Gly Ile Glu Ala Asp Asp Asp Arg Leu Asn Lys Val Ile Ser Glu
                35                  40                 45

Leu Asn Gly Lys Asn Ile Glu Asp Val Ile Ala Gln Gly Ile Gly
                50                  55                 60

Lys Leu Ala Ser Val Pro Ala Gly Gly Ala Val Ala Val Ser Ala
                65                  70                 75

Ala Pro Gly Ser Ala Ala Pro Ala Ala Gly Ser Ala Pro Ala Ala
                80                  85                 90

Ala Glu Glu Lys Lys Asp Glu Lys Lys Glu Glu Ser Glu Glu Ser
                95                  100                105

Asp Asp Asp Met Gly Phe Gly Leu Phe Asp
                110                 115

( 2 ) INFORMATION FOR SEQ ID NO: 4:

( i ) SEQUENCE CHARACTERISTICS:
    ( A ) LENGTH: 106 amino acids
    ( B ) TYPE: amino acid
    ( C ) STRANDEDNESS:
    ( D ) TOPOLOGY: linear (ii) MOLECULE TYPE: protein (iii) FEATURE:
    (A) NAME/KEY: yeast ribosomal P2 protein
    (B) LOCATION: 1...106

(iv) SEQUENCE DESCRIPTION: SEQ ID NO: 4:

```
Met Lys Tyr Leu Ala Ala Tyr Leu Leu Asn Ala Ala Gly Asn
                 5               10              15
Thr Pro Asp Ala Thr Lys Ile Lys Ala Ile Leu Glu Ser Val Gly
                20              25              30
Ile Glu Ile Glu Asp Glu Lys Val Ser Val Leu Ser Ala Leu
                35              40              45
Glu Gly Lys Ser Val Asp Glu Leu Ile Thr Glu Gly Asn Glu Lys
                50              55              60
Leu Ala Ala Val Pro Ala Ala Gly Pro Ala Ser Ala Gly Gly Ala
                65              70              75
Ala Ala Ala Ser Gly Asp Ala Ala Ala Glu Glu Glu Lys Glu Glu
                80              85              90
Glu Ala Ala Glu Glu Ser Asp Asp Asp Met Gly Phe Gly Leu Phe
                95              100             105
Asp
106
```

(2) INFORMATION FOR SEQ ID NO: 5:

(i) SEQUENCE CHARACTERISTICS:
        (A) LENGTH: 20 bases
        (B) TYPE: nucleic acid
        (C) STRANDEDNESS: single
        (D) TOPOLOGY: linear     (ii) MOLECULE TYPE: fluorescein primer     (iii) FEATURE:
        (A) NAME/KEY: Ch2.1 sequencing primer (corresponds to
            position 198-217 of SEQ ID NO: 1)
        (B) LOCATION: 1...20

(iv) SEQUENCE DESCRIPTION: SEQ ID NO: 5:

AGAAGCTTGC CTCCGTTCCC                                            20

(2) INFORMATION FOR SEQ ID NO: 6:

(i) SEQUENCE CHARACTERISTICS:
        (A) LENGTH: 15 bases
        (B) TYPE: nucleic acid
        (C) STRANDEDNESS: single
        (D) TOPOLOGY: linear     (ii) MOLECULE TYPE: fluorescein primer     (iii) FEATURE:
        (A) NAME/KEY: Ch2.1 sequencing primer (corresponds to
            position 312-326 of SEQ ID NO: 1)
        (B) LOCATION: 1...15

(iv) SEQUENCE DESCRIPTION: SEQ ID NO: 6:

AGGAGGAGTC CGACG                                                    15

(2) INFORMATION FOR SEQ ID NO: 7:

(i) SEQUENCE CHARACTERISTICS:
        (A) LENGTH: 30 bases
        (B) TYPE: nucleic acid
        (C) STRANDEDNESS: single (D) TOPOLOGY: linear (i i) MOLECULE TYPE: DNA primer (i i i) FEATURE:
    (A) NAME/KEY: Ch2.1 5'amplification primer
        (positions 9-30 correspond to position 1-22 of SEQ ID NO: 1)
    (B) LOCATION: 1...30

(i v) SEQUENCE DESCRIPTION: SEQ ID NO: 7:

GAATTCTCCG GCAAAAACAC CGTCAAGATG    30

(2) INFORMATION FOR SEQ ID NO: 8:

(i) SEQUENCE CHARACTERISTICS:
        (A) LENGTH: 27 bases
        (B) TYPE: nucleic acid
        (C) STRANDEDNESS: single
        (D) TOPOLOGY: linear     (i i) MOLECULE TYPE: DNA primer     (i i i) FEATURE:
        (A) NAME/KEY: Ch2.1 3'amplification primer
            (designed from lambda ZAP vector)
        (B) LOCATION: 1...27

(i v) SEQUENCE DESCRIPTION: SEQ ID NO: 8:

CTGCAGAATA CGACTCACTA TAGGGCG    27